(12) United States Patent
Cullis-Hill et al.

(10) Patent No.: US 8,293,722 B2
(45) Date of Patent: Oct. 23, 2012

(54) INHIBITION OF CATHEPSIN K ACTIVITY AND THE TREATMENT AND PREVENTION OF DISEASE

(75) Inventors: David Cullis-Hill, Woollahra (AU); Robert Logan Hannon, Normanhurst (AU); Christopher Bond Little, Sydney (AU); Margaret Mary Smith, Thornleigh (AU)

(73) Assignee: Sylvan Pharmaceuticals Pty Ltd., New South Wales (AU)

(*) Notice: Subject to any disclaimer, the term of this patent is extended or adjusted under 35 U.S.C. 154(b) by 550 days.

(21) Appl. No.: 12/330,248

(22) Filed: Dec. 8, 2008

(65) Prior Publication Data
US 2009/0111771 A1    Apr. 30, 2009

Related U.S. Application Data

(63) Continuation of application No. 11/527,725, filed on Sep. 27, 2006, now abandoned.

(51) Int. Cl.
*A01N 43/04*    (2006.01)
*A61K 31/715*   (2006.01)
*C07H 11/00*    (2006.01)
*C07H 13/12*    (2006.01)
*C07H 1/00*     (2006.01)

(52) U.S. Cl. .......................... 514/54; 536/118; 536/123.1
(58) Field of Classification Search .................... 514/54; 536/118, 123.1
See application file for complete search history.

(56) References Cited

U.S. PATENT DOCUMENTS

| 5,145,841 A | 9/1992 | Cullis-Hill |
| 5,470,840 A | 11/1995 | Cullis-Hill |
| 5,668,116 A * | 9/1997 | Cullis-Hill et al. ............. 514/54 |
| 6,593,310 B1 | 7/2003 | Cullis-Hill |
| 2006/0263355 A1 | 11/2006 | Quan et al. |

FOREIGN PATENT DOCUMENTS

WO    WO 2005049028 A1 *    6/2005

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Osteoporosis" from the Mayo Clinic staff [online], [Retrieved on Apr. 25, 2011]. Retrieved from the internet <http://www.mayoclinic.com/health/osteoporosis/DS00128/METHOD=print&DSECTION=all>. Published Nov. 20, 2010.*
Heaney, R.P. (2003) Advances in Therapy for Osteoporosis. Clinical Medicine & Research, vol. 1, No. 2, p. 93-99.*
Krall, E.A., Garcia, R.I., Dawson-Hughes, B. (1996) Increased Risk of Tooth Loss is Related to Bone Loss at the Whole Body, Hip, and Spine. Calcified Tissue International, vol. 59, p. 433-437.*
Dupoirieux, L., Pourquier, D., Picot, M.-C., Neves, M. (1999) The effect of pentosan polysulphate on bone healing of rat cranial defects. Journal of Cranio-Maxillofacial Surgery, vol. 27, p. 314-320.*
Berge, S.M., Bighley, L.D., Monkhouse, D.C. (1977) Pharmaceutical Salts. Journal of Pharmaceutical Sciences, vol. 66, No. 1, p. 1-19.*
Xiao, Y. et al., "Cathepsin K in Adipocyte Differentiation and its Potential Role of the Pathogenesis of Obesity"; The Journal of Clinical Endocrinology & Metabolism, 2006.
Granell, S. et al., Heparin Exacerbates Lung Inflammation in Experimental Acute Pancreatitis through Mobilisation of Xanthine Oxidase; Pancreatology, 2002, vol. 2, pp. 217-361.
Marshall, JL. et al., "Phase I trial of orally administered pentosan polysulfate in patients with advanced cancer": Clinical Cancer Research. vol. 3, Issue 12, pp. 2347-2354, 1997.
Zacharski, L. et al., "The Anticoagulant Heparin: A Possible New Cancer Treatment?", Mar. 2001.
Buhling, F. et al., "Pivotal Role of Cathepsin K in Lung Fibrosis": American Journal of Pathology, vol. 164, No. 6, Jun. 2004.
Chapman, H.A. et al., "Protease Injury in the Development of COPD: Thomas A. Neff Lecture"; Chest—The Cardiolpulmonary and Critical Care Journal: 2000, vol. 117, pp. 295-299.
Li, Z. et al., "Regulation of Collagenase Activities of Human Cathepsins by Glycosaminoglycans"; The Journal of Biological Chemistry, vol. 279, No. 7, Feb. 13, 2004, pp. 5470-5479.
Serveau-Avesque, C. et al., "Active cathepsins B, H, K, L, and S in human inflammatory broncho-alveolar lavage fluids"; Biol. Cell. 2006, vol. 98, pp. 18-22.
Wang, Z. et al., "Interferon γ Induction of Pulmonary Emphysema in the Adult Murine Lung"; J. Exp. Med, Dec. 4, 2000 vol. 192, No. 11.
Little, L. "Cathepsin K Blocker Promising for Osteoporosis"; Medscape Medical News, 2005.
Li. Z. et al., "Collagenase Activity of Cathepsin K Depends on Complex Formation with Chondroiton Sulfate"; J. Biol. Chem., vol. 277, Issue 32, pp. 28669-28676, Aug. 9, 2002.
Han. GL. et al., "Expression of cathepsin K and IL-6 mRNA in root-resorbing tissue during tooth movement in rats"; PubMed, Jul. 2004, vol. 39, Issue 4, pp. 320-323.
Linsuwanont, B. et at, "Localization of cathepsin K in bovine odontoclasts during deciduous tooth resoption"; Calcif Tissue Int., Feb. 2002, vol. 70, No. 2, pp. 127-133.
Mandelin, J. et al., "Pseudosynovial fluid from loosened total hip prosthesis induces osteoclast formation"; J Biomed Mater Res B Appl Biomater, Jul. 2005, vol. 74, No. 1, pp. 582-588.
Oui, J. et al., "Simultaneous labeling of mast cell proteases mRNAs at the bone-implant interface of aseptically loosened hip implants"; J Ortho Res, Jul. 2005, vol. 23, No. 4, pp. 942-948.
Oshiro, T. et al., "Immunolocalization of vacuolar-type H+-ATPase, cathepsin K, matrix metalloproteinase-9, and receptor activator of NFkappaB ligand in odontoclasts during physiological root resorption of human deciduous teeth"; Anat Rec, Nov. 1, 2001, vol. 264, No. 3, pp. 305-311.
Shen, Z. et al., "The role played by cell-substrate interactions in the pathogenesis of osteoclast-mediated peri-implant osteolysis"; Arthritis Res Ther, 2006, vol. 8, No. 3, R70.
Takagi, M. at al., Cathepsin G and alpha 1-antichymotrypsin in the local host reaction to loosening of total hip prostheses; J Bone Joint Surg Am, Jan. 1995, vol. 77, No. 1, pp. 16-25.

(Continued)

*Primary Examiner* — Scarlett Goon
(74) *Attorney, Agent, or Firm* — Browdy and Neimark, PLLC

(57) ABSTRACT

The present invention provides a candidate compound that is suitable for use in methods of treating animals (preferably mammals) and in the preparation of a medicament, wherein the candidate compound down regulates Cathepsin K activity.

3 Claims, 6 Drawing Sheets

OTHER PUBLICATIONS

Tsuji, Y. et al., "Expression of cathepsin K mRNA and protein in odontoclasts after experimental tooth movement in the mouse maxilla by in situ hybridization and immunoelectron microscopy"; Cell Tissue Res, Mar. 2001, vol. 303, No. 3, pp. 359-369.

Tyrrell, DJ. et al., "Heparin in inflammation: potential therapeutic application beyond anticoagulation"; Adv Pharmacol, 1999, vol. 46, pp. 151-208.

Chiellini, C. et al., "Identification of cathepsin K as a novel marker of adiposity in white adipose tissue"; J Cell Physiol, May 2003, vol. 195, No. 2, pp. 309-321.

Zimmermann, G. et al. "Generation by Bacterial Lipopolysaccharide (LPS) as Possible Mechanism of Infection-associated Bone Resorption", Basic Research, Bacteriology II, 25th Annual Meeting of the European Bone and Joint Infection Society, May 25-27, 2006 in Budapest, Hungary.

Srivastava AK. et al., "Pentosan polsulfate, a potent anti HIV and anti tumor agent, inhibts protein serine/threonine and tyrosine kinases": Mol Cell Biochem, Mar. 24, 1993, vol. 120, No. 2, pp. 127-133.

Schwartz, CF. et al., "Increased rat cardiac altograft survival by the glycosaminoglycan pentosan polysulfate"; J Surg Res. Sep. 1999, vol. 86, No. 1, pp. 24-28.

Bartglen, W. et al.. "Significant of heparin-binding growth factor expression on cells of solid pediatric tumors", Journal of Pediatric Surgery, vol. 38, No. 9, pp. 1296-1304, 2003.

Gohji, K. et al., "Human heparanase: roles in invasion and metastasis of cancer"; Hinyokika Kiyo, vol. 46, No. 10, pp. 757-762, 2000.

Hejna, M. et al.,"Inhibition of metastases by anticoagulants": J Natl Cancer Inst; vol. 91, No. 1, pp. 22-36, 1999.

Herbert, J. et al., "Activity of pentosen polysulphate and derived compounds on vascular endothelial cell proliferation and migration induced by acidic and basic FGF in vitro"; Biochemical Pharmacology. vol. 37, No. 22, pp. 4281-4288. 1998.

Kenagy, R.D. et al., "Heparin inhibits the induction of three matrix metalloproteinases (stromelysin, 92-kD gelatinase, and collagenase) in primate arterial smooth muscle cells"; Journal of Clinical Investigation, vol. 93, pp. 1987-1993, 1994.

Lebeau, B. et al., "Subcutaneous heparin treatment increases survival in small cell lung cancer"; Cancer, vol. 74. No. 1, pp. 38-45, 1994.

McCleskey, S.W. et al., "Effects of AGM-1470 and pentosan polysuiphate on tumorigenicity and metastasis of FGF-transfected MCF-7 cells"; British Journal of Cancer, vol. 73, pp. 1053-1062, 1996.

Motlekar N.A. et al., "The quest for non-invasive delivery of bioactive macromolecules: a focus on heparins"; J Control Release, vol. 113, No. 2, pp. 91-101, 2006.

Mucha, S. et al., "Effects of Pentosan polysulfate sodium on the estrogen-induced pituitary prolactinoma in Fischer 344 rats"; Oncology reports, vol. 9, pp. 1385-1389, 2002.

Nguyen, N.M. et al., "Pentosan inhibits angiogenesis in vitro and suppresses prostate tumor arowth in vivo": Anticancer Research, vol. 13, No. 6a, pp. 2143-2147, (1993).

Norrby, K. et al., "A 5.0-kD heparin fraction systemically suppresses VEGF165-mediated angiogenesis"; Int J Microcirc Clin Exp, vol. 17, No. 6, pp. 314-321, 1997.

Parish, C.R. et al., Identification of sulfated oligosaccharide-based inhibitors of tumor growth and metastasis using novel in vitro assays for angiogenesis and heparanase activity, Cancer Res, vol. 59, No. 14, pp. 3433-3441, 1999.

Pienta, K.J. et al., "Effect of pentosan, a novel cancer chemotherapeutic agent, on prostate cancer cell growth and motility"; Prostate, vol. 20, No. 3, pp. 233-241, 1992.

Pluda, J.M. at al., "Administration of pentosan polysulfate to patients with human immunodeficiency virus-associated Kaposi's Sarcoma"; Journal national Cancer Institute, vol. 85, No. 19, pp. 1585-1592, 1993.

Rha, S.Y. et al., "Comparison of biological phenotypes according to midkine expression in gastric cancer cells and their autocrine activities could be modulated by pentosan polysulfate"; Cancer Letters, vol. 118, pp. 37-46, 1997.

Smorenburg, S.M. et al., The Complex effects of heparins on cancer progression and metastasis in experimental studies; Pharmacological Reviews, vol. 53, No. 1, pp. 93-105, 2001.

Soker, S. et al., "Variations in the size and sulfation of heparin modulate the effect of heparin on the binding of VEGF165 to its receptors"; Biochem Biophys Res Commun., vol. 203. No. 2, pp. 1339-1347, 1994.

Wellstein, A. et al., "Tumor growth dependent on Kaposis sarcoma-derived fibroblast growth factor inhibited by pentosan polysulfate"; Journal of the National Cancer Institute, vol. 83, No. 10, pp. 716-720, 1991.

Yunmbam, M.K et al., "Inhibition of breast cancer in nude mouse model by anti-angiogenesis"; Oncology Reports, vol. 5, No. 6, pp. 1431-1437, 1998.

Yunmbam, M.K. et al,, "The bacterial polysaccharide tecogalan blocks growth of breast cancer cells in vivo"; Oncology Reports, vol. 8, pp. 161-164, 2001.

Zugmaier, G. et al.. "Inhibition by pentosan polysulfate (PPS) of heparin-binding growth factors released from tumor cells and blockage by PPS of tumor growth in animals"; Journal of the National Cancer Institute, vol. 264, pp. 16411-16420, 1992.

Krell, E.A., Garcia, R.I., Dawson-Hughes, B. (1996) Increased Risk of Tooth Loss is Related to Bone Loss at the Whole Body, Hip, and Spine. Calcified Tissue International, vol. 59, p. 433-437.

* cited by examiner

INHIBITION OF CATHEPSIN K ACTIVITY AND THE TREATMENT AND PREVENTION OF DISEASE

FIELD OF INVENTION

The invention relates to regulating the expression or activity of cathepsin K in an animal in need thereof. More particularly the invention relates to the treatment and prevention of diseases in which the activity or expression of cathepsin K is up regulated.

BACKGROUND OF THE INVENTION

Cathepsin K is a lysosomal enzyme with a typical acid pH (5.5) optimum. The importance of this enzyme in intracellular (lysosomal) collagenolytic activity has been demonstrated by the accumulation of endocytosed collagen fibrils in fibroblasts treated with a cathepsin K inhibitor in vitro. However, cathepsin K also plays a significant role in extracellular type I collagenolysis in the phagolysosome-like resorption compartment of active osteoclasts in bone. Inhibition of cathepsin K in vitro and in vivo significantly decreases osteoclastic bone resorption. Pycnodysostosis (PD), a genetic disorder in humans characterised by osteosclerosis and short stature is due to a deficiency in cathepsin K activity. Individuals affected with PD have significantly decreased bone collagen turnover, suggesting that cathepsin K is the principle enzyme responsible for physiological bone matrix turnover.

In pathological conditions such as in post-menopausal osteoporosis (and ovariectomy models in rats) and other metabolic bone disorders like Paget's disease, the excessive bone resorption is also associated with collagen turnover by cathepsin K. Furthermore, increased bone turnover in rheumatoid and osteoarthritis is associated with elevated collagen cleavage by cathepsin K.

In contrast, bone lysis and collagen release in cancer metastasis to bone is thought to be predominantly due to enhanced metallo matrix protein (MMP) activity. Similarly, while increased cathepsin K expression in lysosomes of synovial fibroblasts and chrondrocytes has been observed in arthritis, a direct role in extracellular cartilage matrix degeneration has not been demonstrated. In contrast, MMP-driven articular cartilage collagen breakdown in vitro and in arthritic joints has been well documented. Taken together, these data indicate that cathepsin K plays a central role in type I collagenolysis and bone remodelling in physiological and certain pathological conditions. Therefore, mechanisms to inhibit cathepsin K activity represent excellent targets for the treatment of excessive bone turnover.

Although once thought to reside exclusively in osteoclasts, Cathepsin K expression has been discovered in a significant fraction of human breast cancers, prostate cancer and associated metastases.

Furthermore, activation of human pulmonary fibroblasts in primary cell cultures has been found to lead to an increased activity of Cathepsin K and to increase intracellular collagenolytic activity suggesting that Cathepsin K plays a pivotal role in lung matrix homeostasis under physiological and pathological conditions.

SUMMARY OF THE INVENTION

In work leading to the present invention, the inventors sought to provide an inhibitor of Cathepsin K activity that is suitable for administration to animals and in particular mammals. To that end, the inventors have surprisingly identified that an oversulfated polysaccharide such as, for example pentosan polysulfate (PPS) and more particularly xylopyranose polysulfate (XPS) can significantly down regulate Cathepsin K activity or expression, as well as inhibit osteoclast formation and osteoclast function.

The present invention therefore provides a candidate compound that is suitable for use in methods of treating animals (preferably mammals) and in the preparation of a medicament, wherein the candidate compound down regulates Cathepsin K activity.

In one aspect the present invention provides methods for treating or preventing bone resorption in an animal in need thereof, the method comprising the step of administering an effective amount of an oversulfated polysaccharide.

In a preferred embodiment the oversulfated polysaccharide is pentosan polysulfate, more preferably xylopyranose polysulfate. Preferably the pentosan polysulfate is calcium pentosan polysulfate, more preferably calcium xylopyranose polysulfate.

As used herein, the term "bone resorption" refers to a loss of bone through increased breakdown via osteoclasts or other mechanism causing a reduction in bone mass.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The Cathepsin K inhibitors identified by the present inventors are particularly useful in pathological processes involving excess osteoclast activation and bone resorption, such as bone metastases or multiple myeloma.

Accordingly, the present invention provides a method of treating or preventing bone resorption associated with bone metastases or multiple myeloma in a mammal in need of such treatment, comprising the step of administering an effective amount of an oversulfated polysaccharide.

The Cathepsin K inhibitors identified by the present inventors are also useful in other processes involving bone matrix resorption. For example, the Cathepsin K inhibitors are useful in the treatment and prevention of tooth root resorption, and osteolysis associated with surgical implants and joint replacement.

Accordingly the present invention provides a method for treating or preventing bone resorption associated with tooth root resorption in a mammal in need of such treatment, comprising the step of administering an effective amount of an oversulfated polysaccharide.

Resorption of a part of the root of a tooth may be either internal (pulpal) or external.

The present invention further provides a method for treating or preventing excess bone resorption associated with osteolysis in a mammal in need of such treatment, comprising the step of administering an effective amount of an oversulfated polysaccharide.

Osteolysis refers to an active resorption or dissolution of bone tissue as part of an ongoing disease process. While bone resorption is commonly associated with many diseases, the term osteolysis generally refers to a problem common to artificial joint replacements such as total hip replacements, total knee replacements and total shoulder replacements. In a total hip replacement, for example, the particles worn off the gliding surface of the ball and socket joint often cause osteolysis. As the body attempts to clean up these loose particles of plastic or metal, the bone grows away from the implant, causing it to loosen.

The present invention further provides a candidate compound suitable for use in the treatment of or amelioration of bone defects. Defects include, for example, post traumatic injuries such as fractures or defects of the bone after a bone resection or removal of a growth (such as a cyst) in the bone. In one embodiment the candidate compound is useful in the treatment of delayed healing of bone fractures and infection associated delayed healing or non-unions of fractures.

In a preferred embodiment the oversulfated polysaccharide is pentosan polysulfate, more preferably calcium pentosan polysulfate. In a more preferred embodiment the oversulfated polysaccharide is xylopyranose polysulfate, more preferably calcium xylopyranose polysulfate.

In another aspect the present invention provides methods for treating or preventing tissue destruction associated with inflammation of an airway or lung in an animal in need thereof, the method comprising the step of administering an effective amount of an oversulfated polysaccharide.

In a preferred embodiment the oversulfated polysaccharide is pentosan polysulfate, more preferably calcium pentosan polysulfate. In a more preferred embodiment the oversulfated polysaccharide is xylopyranose polysulfate, more preferably calcium xylopyranose polysulfate.

Inflammation of a lung or airway usually involves infiltration of one or more leucocytes including neutrophils, eosinophils, lymphocytes and monocytes but can also involve macrophages, mast cells or basophils. In inflammation, there is an expression of a wide array of catabolic enzymes including proteases. Those lesions expressing the protease Cathepsin K have a uniquely enhanced collagen cleaving activity which opens up further targets in tissues for other enzymes and causes tissue destruction. Conditions which involve inflammation include, for example, chronic obstructive pulmonary diseases with or without acute infections or worsening of inflammation, lung fibrosis, allergic diseases and asthma. This also includes inflammation in the airways including upper airways caused by allergy or infection or other diseases.

Accordingly the present invention provides a method for treating or preventing tissue destruction associated with chronic obstructive pulmonary disease (COPD) in a mammal in need of such treatment, comprising the step of administering an effective amount of an oversulfated polysaccharide. In one embodiment the COPD is related to emphysema.

In another embodiment the present invention provides a method for treating or preventing tissue destruction associated with lung fibrosis in a mammal in need of such treatment, comprising the step of administering an effective amount of an oversulfated polysaccharide.

In yet another embodiment the present invention provides a method for treating or preventing obesity in a mammal in need of such treatment, comprising the step of administering an effective amount of an oversulfated polysaccharide.

In a preferred embodiment the oversulfated polysaccharide is pentosan polysulfate, more preferably calcium pentosan polysulfate. In a more preferred embodiment the oversulfated polysaccharide is xylopyranose polysulfate, more preferably calcium xylopyranose polysulfate.

The methods of the present invention comprise administration of an effective amount of the candidate compound to the individual in need thereof. The present invention further provides for the use of the candidate compound alone or together with a suitable excipient in the preparation of a medicament.

The term "effective amount" refers to a therapeutically effective amount and refers to an amount of the compound to treat, ameliorate, or prevent a desired disease or condition, or to exhibit a detectable therapeutic or preventative effect. The effect can be detected by, for example, chemical markers. Therapeutic effects also include reduction in physical symptoms, such as decreased bone resorption decreased tissue destruction and even improved condition of the bone or tissue. The precise effective amount for a situation is determined by routine experimentation and is within the judgement of the clinician.

The compound is administered preferably in an amount such as to produce a concentration of the compound in the blood of 0.01 to 100 micrograms/ml plasma, for example 0.1 to 50 micrograms per ml plasma. Typically, administration of about 0.1-30 mg/kg body weight of the compound will produce a plasma concentration in the range of 0.1-100 micrograms/ml. The compound can be administered in a single dose or in multi-dosage form, at one time or intermittently to reduce any effects of toxicity.

Any administration known in the art may be used. In one preferred embodiment the candidate compound is administered systematically (by injection). One preferred systemic dose is about 1-5 mg/kg, more preferably 2 mg/kg body weight.

In another embodiment the candidate compound is administered orally. A preferred oral dose is about 10-30 mg/kg, more preferably about 20 mg/kg body weight.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

DETAILED DESCRIPTION

Polysulfated Polysaccharides

Figure 1:
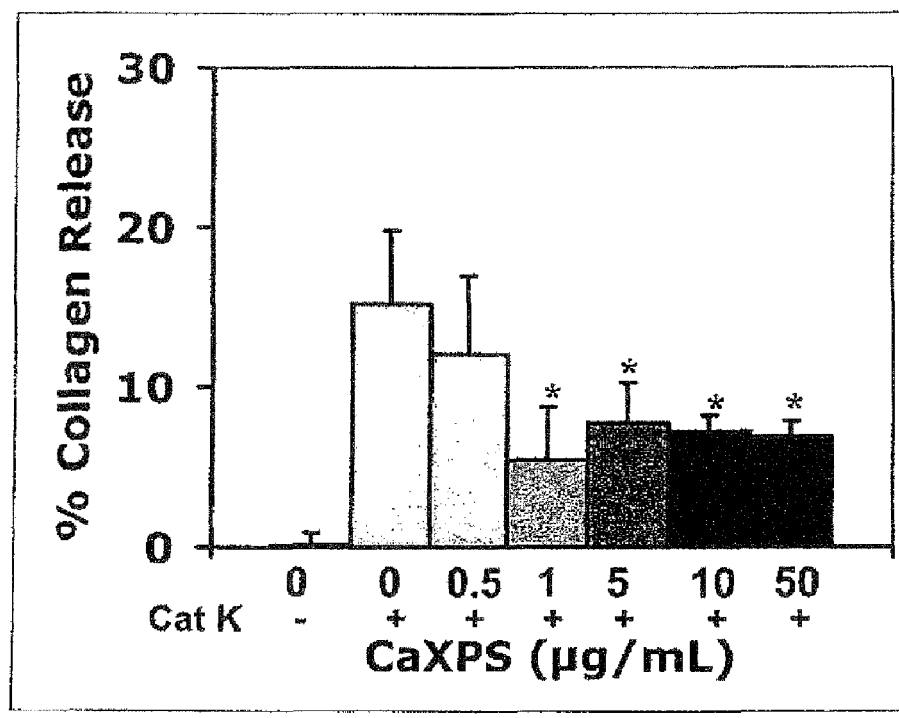
FIG. 1 is a bar graph for the results of dose response of CaXPS on Cathepsin K mediated release of bone collagen (Mean±SD). *=$p<0.05$ vs no CaXPS.

Xylopyranose polysulfate (XPS) which is a semi-synthetic derivative of beechwood, is one example of an oversulfated polysaccharide useful in the present invention.

Pentosan polysulfates (PPS) and, more particularly, xylopyranose polysulfates are available as an alkali metal salt or alkaline earth metal salt, for example, comprising calcium or sodium salt, or transition metals such as copper and zinc and noble metals such as platinum. Accordingly, the particular complexing ions may be selected from the group consisting of the alkali metals, e.g. $Na+$ and $K+$, alkaline earth metals, e.g. $Ca2+$, $Zn2+$, $Mg2+$, $Ba2+$, as well as $Ag+$, $Pb2+$, $Cu2+$, $Au2+$, $Pd2+$, $Pd4+$, $Pd4+$, $Pd2+$, trivalent metal ions, and quaternary ammonium compound complexes. Examples of the latter compound are pyridinium chloride, tetraalkyl ammonium chloride, chorine chloride, cetylpyridinium chloride, N-cetyl-N,N,N-trialkylammonium chloride or their derivatives. The most preferred of these are the divalent alkaline earth metals, preferably calcium, and magnesium and most preferable is the calcium complex. Preparation of the polysulfate polysaccharide-metal complexes is described in detail in U.S. Pat. No. 5,668,116, the entire disclosure of which is incorporated herein by reference.

Other polysulfated polysaccharides included within the scope of the invention are, for example, polysulfated dextran and derivatives thereof polysulfated cyclodextrin, sulfated heparin, sulfated mannose and mannose derivatives, xylan, polysulfated chondroitin, dermatan and hyaluronic acid. Further examples are polysulfated polysaccharide derivatives of homopolysaccharides or heteropolysaccharides which can be linear or branched. As described above, complexes are also formed between these polysulfated polysaccharides and multivalent metal ions, $Ag+$ and $Au+$, and quaternary ammonium compound complexes.

The sugars may come from but are not limited to pentoses or hexoses such as galactose, mannose, glucose, rhanose, fructose, sorbose, xylose, D-arabinose, ribose, L-arabinose, glucuronic acid and their derivatives.

The term oversulfated refers to the compound having a sulfate group attached to all oxygen sites that are available for sulfation. For example, PPS contains approximately two sulfate groups per carbohydrate monomer, Due to uronic acid side groups on PPS, the degree of sulfation on PPS is approximately 1.8.

Sulphation of polysaccharides is described in detail in U.S. Pat. No. 5,668,116, the entire disclosure of which is incorporated herein by reference.

The compound may be administered to the patient alone or in combination with a pharmaceutically acceptable carrier.

Method of Administration

The administration according to the use and method of the present invention may be any administration known in the art as may easily be recognised by the skilled person according to the individual situation. Accordingly, the administration may be selected from systemic administration; injection into tissue or into a body cavity including joints; implantation into tissue or into a body cavity; topical application to the skin or to any gastrointestinal surface or to a mucosal surface including the lining of body cavities. The administration may be selected from parenteral administration, including intraperitoneal administration, intrathecal administration, systemic administration, local administration, topical administration, transmucosal administration, transdermal administration and oral administration.

One preferred method of administration according to the method of the invention is by the oral route. Another preferred method of administration is by infiltration for treatments around a tooth root, prosthesis or bone defects. Infiltration can include either topical application into and around the lesion or alternatively local injection into and around the lesion. In yet another embodiment the preferred mode of administration is systemic, i.e. by iv, im or subcutaneous injection. For injection, the carrier would typically be for example normal sterile physiological saline.

Pharmaceutical Formulations and Compositions

These are intended to include pharmaceutical compositions, cosmetics and cosmeceuticals.

For the administration to an individual (an animal or a human) the substances are preferably formulated into a pharmaceutical composition containing the target compound and, optionally, one or more pharmaceutically acceptable excipients.

The compositions may be in the form of a solid, semi-solid or fluid composition such as, but not limited to, for example, bioabsorbable patches, drenches, dressings, hydrogel dressings, hydrocolloid dressings, films, foams, sheets, bandages, plasters, delivery devices, implants, powders, granules, granulates, capsules, agarose or chitosan beads, tablets, pills, pellets, microcapsules, microspheres, nanoparticles, sprays, aerosols, inhalation devices, gels, hydrogels, pastes, ointments, creams, soaps, suppositories, vagitories, tooth paste, solutions, dispersions, suspensions, emulsions, mixtures, lotions, mouthwash, shampoos, enemas.

A pharmaceutical composition comprising an active substance serves as a drug delivery system. In the present context the term "drug delivery system" denotes a pharmaceutical composition (a pharmaceutical formulation or a dosage form) which upon administration presents the active substance to the body of a human or an animal and if necessary facilitates the presentation of the active substance to the appropriate site of treatment. Thus, the term "drug delivery system" embraces plain pharmaceutical compositions such as, e.g., creams, ointments, liquids, powders, tablets, etc. as well as more sophisticated formulations such as sprays, plasters, bandages, dressings, devices, etc.

The compositions may be formulated according to conventional pharmaceutical practice, see, e.g., "Remington: The science and practice of pharmacy" 20th ed. Mack Publishing, Easton Pa., 2000 ISBN 0-912734-04-3 and "Encyclopedia of Pharmaceutical Technology", edited by Swarbrick, J. & J. C. Boylan, Marcel Dekker, Inc., New York, 1988 ISBN 0-8247-2800-9.

Apart from the candidate compound, a pharmaceutical composition for use according to the invention may comprise pharmaceutically or cosmetically acceptable excipients.

The choice of pharmaceutically acceptable excipients in a composition for use according to the invention and the optimum concentration thereof cannot generally be predicted and must be determined on the basis of an experimental determination thereof. Also whether a pharmaceutically acceptable excipient is suitable for use in a pharmaceutical composition is generally dependent on which kind of dosage form is chosen. However, a person skilled in the art of pharmaceutical formulation can find guidance in e.g., "Remington: The science and practice of pharmacy" 20th ed. Mack Publishing, Easton Pa., 2000 ISBN 0-912734-04-3.

A pharmaceutically acceptable excipient is a substance, which is substantially harmless to the individual to which the composition will be administered. Such an excipient normally fulfils the requirements given by the national drug agencies. Official pharmacopoeias such as the British Pharmacopeia, the United States of America Pharmacopeia and the European Pharmacopeia set standards for well-known pharmaceutically acceptable excipients.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions

For systemic application, the compositions according to the invention may contain conventionally non-toxic pharmaceutically acceptable carriers and excipients for example including microspheres and liposomes.

The compositions for use according to the invention include all kinds of solid, semisolid and fluid compositions. Compositions of particular relevance are e.g. solutions, suspensions, emulsions, gels, implantation tablets and implants.

The pharmaceutically acceptable excipients may include solvents, buffering agents, preservatives, humectants, chelating agents, antioxidants, stabilizers, emulsifying agents, suspending agents, gel-forming agents, diluents, disintegrating agents, binding agents, lubricants and wetting agents. For examples of the different agents see below.

Topical, Transmucosal and Trans-Dermal Compositions:

For application to the mucosa or the skin, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, resoriblets, suppositories, enema, pessaries, moulded pessaries, vaginal capsules, vaginal tablets, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, suppository bases, penetration enhancers, perfumes, skin protective agents, diluents, disintegrating agents, binding agents, lubricants and wetting agents. For examples of the different agents see below.

For application to the mucosa or the skin, the compositions for use according to the invention may contain conventionally non-toxic pharmaceutically acceptable carriers and excipients including microspheres and liposomes.

Oral Compositions:

The composition for use according to the invention includes all kinds of solid, semi-solid and fluid compositions. Compositions of particular relevance are e.g. solutions, suspensions, emulsions, uncoated tablets, modified-release tablets, gastro-resistant tablets, orodispersible tablets, effervescent tablets, chewable tablets, soft capsules, hard capsules, modified release capsules, gastro-resistant capsules, uncoated granules, effervescent granules, granules for the preparation of liquids for oral use, coated granules, gastro-resistant granules, modified-release granules, powders for oral administration and powders for the preparation of liquids for oral use.

The pharmaceutically acceptable excipients may include solvents, buffering agents, preservatives, humectants, chelating agents, antioxidants, stabilizers, emulsifying agents, suspending agents, gel-forming agents, diluents, disintegrating agents, binding agents, lubricants, coating agents and wetting agents. For examples of the different agents see below.

Examples of Various Agents:

Examples of solvents are but not limited to water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsolixanes, and mixtures thereof.

Examples of buffering agents are but not limited to citric acid, acetic acid, tartaric acid, lactic acid, hydrogenphosphoric acid, diethylamine etc.

Examples of preservatives for use in compositions are but not limited to parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are but not limited to glycerine, propylene glycol, sorbitol, lactic acid, urea, and mixtures thereof.

Examples of chelating agents are but not limited to sodium EDTA and citric acid.

Examples of antioxidants are but not limited to butylated hydroxy anisole (BHA), ascorbic acid and derivatives thereof, tocopherol and derivatives thereof, cysteine, and mixtures thereof.

Examples of emulsifying agents are but not limited to naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are but not limited to celluloses and cellulose derivatives such as, e.g. carboxymethylcellulose, hydroxyethylcellulose, hydroxypropylcellulose, hydroxypropylmethylcellulose, carraghenan, acacia gum, arabic gun, and mixtures thereof.

Examples of gel bases and viscosity-increasing are but not limited to liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives, water-swellable hydrocolloids, carragenans, hyaluronates (e.g. hyaluronate gel optionally containing sodium chloride), and alginates including propylene glycol alginate.

Examples of ointment bases are but not limited to beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic ointment bases are but not limited to paraffins, vegetable oils, animal fats, synthetic glycerides, waxes, lanolin, and liquid polyalkylsiloxanes.

Examples of hydrophilic ointment bases are but not limited to solid macrogols (polyethylene glycols).

Examples of powder components are but not limited to alginate, collagen, lactose, powder which is able to form a gel when applied to a wound (absorbs liquid/wound exudates).

Examples of diluents and disintegrating agents are but not limited to lactose, saccharise, emdex, calcium phosphates, calcium carbonate, calcium sulphate, mannitol, starches and microcrystalline cellulose.

Examples of binding agents are but not limited to saccharise, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Examples of wetting agents are but not limited to sodium laurylsulphate and polysorbate 80.

Examples of lubricants are but not limited to talcum, magnesium stearate, calcium stearate, silicium oxide, precirol and polyethyleneglycol.

Examples of coating agents are but not limited to hydroxypropylcellulose, hydroxypropylmethylcellulose, polyvinylpropylidone, ethylcellulose and polymethylacrylates.

Examples of suppository bases are but not limited to oleum cacao, adeps solidus and polyethylenglycols.

The candidate compound is present in the medicament in an amount of 0.001-99%, typically 0.01-75%, more preferably 0.1-20%, and especially 1-10% by weight of the medicament.

The Role of Cathepsin K in Disease
Cathepsin K is Expressed in Human Breast Carcinoma In patients with bone metastases, bone loss is the consequence of a dissociated process combining excessive bone resorption and inhibited bone formation.

Invading cells in bone metastases of breast cancer have been found to express Cathepsin K. Immunolocalization of Cathepsin K in breast tumor bone metastasis has revealed that the invading breast cancer cells expressed this protease, albeit at a lower intensity than in osteoclasts. Expression of Cathepsin K mRNA has been confirmed by reverse transcription PCR and Southern analysis in a number of human breast cancer cell lines and in primary human breast tumors and their metastasis. Thus, the present invention provides a novel candidate compound suitable for use in a medicament for preventing the invasive potential of breast cancer cells, in particular those that degrade bone matrix proteins, and treating or preventing bone resorption associated with breast cancer.

Prostate Cancer

Prostate cancer is often also associated with bone metastasis, which cause much of the morbidity associated with prostate cancer. Prostate cancer bone metastasis exhibit increases in both bone formation and resorption. It has been found that Cathepsin K is expressed in bone metastasis at a significantly higher rate that in primary prostate cancer. Lesions associated with prostate cancer generally exhibit increased bone formation and resorption. Increased bone resorption may release factors from the extra cellular matrix that contribute to tumor growth. Prostate cancer expressed Cathepsin K is postulated to contribute to the invasive potential of prostate cancer, while increased expression in bone metastasis is consistent with a role in matrix degradation. Therefore, the present invention provides a novel candidate compound suitable for use in a medicament for treating or preventing the invasive potential of prostate cancer, and in particular treating or preventing bone resorption associated with prostate cancer.

Lung Cancer

In study a of osteoclastic functions in osteolytic metastasis of lung cancers, bone resorping osteoclasts were reactive for both cathepsin K and MMP-9, whereas the osteoclasts in the stromal tissue of the tumour nests showed only MMP-9 immunoreactivity. Osteoclasts appeared to easily migrate in the stromal tissue and to be involved in the alteration of microenvironment of osteolytic metastasis by extracellular matrix degradation, as well as bone resorption.

Giant Cell Tumor

Giant cell tumor (GCT) of bone is a neoplasm of bone characterized by a localized osteolytic lesion. It has been found that cathepsin K is the principal protease in giant cell tumor of bone, and it is suggested that osteoclast-like giant cells are responsible for osteolysis. Inhibition of cathepsin K or its associated proton-pump would provide a new therapeutic opportunity for GCT, and accordingly the present invention provides a novel method for treating or preventing GST of bone.

Chordoma

Invasive growth of chordoma is accompanied by severe destruction of adjacent bone tissue, a fact that requires high proteolytic activity at the tumor invasion fronts.

Enzyme histochemistry indicates a strong cell-associated cathepsin K activity in invasive tumor components. Studies have shown that the significant expression and activity of cathepsin K in chordoma and implicates an important role of the protease in the infiltrative growth of the tumor.

Thyroid Carcinoma

Expression of Cathepsin K in multinucleated giant cells (MGC) of the anaplastic carcinoma of the thyroid gland is postulated to contribute to the invasive behaviour of this tumour thus promoting metastatic ability and destruction of the cartilaginous trachea. The present invention provides a novel method for treating or preventing MGC of the carcinoma of the thyroid gland.

Multiple Myeloma

Multiple myeloma is characterized by the accumulation of clonal malignant plasma cells in the bone marrow, which stimulates bone destruction by osteoclasts and reduces bone formation by osteoblasts. A challenge for treating multiple myeloma is discovering drugs targeting not only mycloma cells but also osteoclasts and osteoblasts. In cultures of human primary monocytes, it has been found that there is an up-regulation of cathepsin K gene expression. Cathepsin K is considered to be a target for treating multiple myeloma and its effects on bone.

Tooth Root Loosening

Investigations of the expression and localisation of Cathepsin K in root-resorping tissue indicates that expression of Cathepsin K mRNA increases in root-resorping tissue compared with the normal peridontum. It is believed that ondotoclast in the root-resorping tissue expressed Cathepsin K mRNA that participates in proteolysis during root resorption. Evidence suggests that the cellular mechanisms of physiological root resorption appear to be quite similar to those of osteoclastic bone resorption.

The distribution of Cathepsin K in ondotoblasts has been found to be similar to that previously seen in osteoclasts. Furthermore, Cathepsin K-positive fibril-like structures were found in the vacuoles of fibroblasts, Cathepsin K is suggested to take a part in the degradation of the dentin matrix (type I collagen fibrils and non-collagenous protein) of the tooth root, and in subsequent intracellular degradation of endocytosed fragmented fibril-like structure in endolysosomes.

Surgical Implant Loosening

Prosthetic wear debris-induced peri-implant osteolysis is a major cause of aseptic loosening after total joint replacement. Cathepsin K and tartrate-resistant acid phosphatase were highly expressed in both mononucleated and multinucleated cells associated with the bone surface. Findings suggest that cells expressing the full repertoire of osteoclast phenotypic markers are involved in the pathogenesis of peri-implant osteolysis after total joint replacement. In one study it was found that interface tissue between the bone and loosening total hip implant is acidic and highly osteolytic. It is characterized by the formation of Cathepsin K positive foreign body giant cells. The multinuclear cells induced with pseudosynovial fluid contained active cathepsin K protein and were capable of bone matrix resorption in vitro. The cells were shown to express osteoclast phenotype markers, such as mRNA for cathepsin K, TRAP and calcitonin receptor.

Infection—Associated Bone Resorption

Persistent infection can participate in delayed or non-unions of long bone fractions. In the context of bacterial infection the generation of osteoclasts may be enhanced. Genes specific for osteoclasts such as tartrate resistant acid phosphatase (TRAP) and Cathepsin K are found to be upregulated in cells of a promonocytic cell line, U937 which were differentiated to monocytes. Local bacterial infections with shedding of bacterial lipopolysaccharide may create a microenvironment promoting the generation of bone resorbing cells. This in turn could contribute to the infection-associated delayed healing or non-unions of fractures. The present invention provides a method for treating and promoting healing in delayed or non-unions of long bone fractions.

Delay or non-union of bones can also occur for example after trauma and without the presence of an infectious element.

Pulmonary Conditions

Inflammation of airways and lung is often associated with swelling of airway and lung tissue and infiltration of airway and lung tissue with leucocytes including neutrophils, eosinophils or basophils and mast cells. This is well established and seen in extraordinary common conditions such as common cold, airway infection, and pulmonary infections, but also in conditions associated with allergy including allergic rhinitis, asthma or other allergic conditions. Moreover, this is also seen in acute diseases associated with inflammation of lung and airways as well as in chronic obstructive pulmonary disease including chronic bronchitis, adult chronic bronchitis and emphysema. The course of COPD is characterized by intermittent exacerbations of the disease. In an exacerbation, there is also a significant influx of eosinophils into the tissue contributing to the inflammation.

Lung Fibrosis

Lung fibrosis is characterized by tissue remodelling resulting from an imbalance between synthesis and degradation of extracellular organic matrices. In lung tissue cathepsin K transcription is the most strongly upregulated in response to silica, and this upregulation is related to the fibrotic process. Pulmonary macrophages and fibroblasts have been identified as cathepsin K overproducing cells in the lung of silicotic mice. Interstitial fibrosis of the lung is a final common pathway of many different lung diseases, such as idiopathic interstitial pneumonitis (idiopathic pulmonary fibrosis) and granulomatous diseases (sarcoidosis). Fibrotic areas are also commonly found in patients suffering from chronic obstructive pulmonary disease. There is evidence to support that cathepsin K has a specific role in the development of lung fibrosis Higher cathepsin K-mediated collagenolytic activity in fibroblasts of fibrotic lungs indicates that cathepsin K is functionally active and is crucial to degrade ECM proteins. Modulating the expression and activity of cathepsin provides a new approach for the treatment and/or prevention of lung fibrosis.

Chronic Obstructive Pulmonary Disease/Emphysema

Recent studies suggest that in the setting of inflammation, such as induced by cigarette smoking, cells that do not normally express cathepsin K begin to do so and in doing so may act like osteoclasts. Studies in human vascular smooth muscle cells exemplify this point. Vascular smooth muscle cells do not normally express with cathepsin S or K in the setting of evolving atherosclerosis, however, there is marked upregulation of both enzymes in medial and nonintimal smooth muscle cells.

Obesity

In obesity, adipocytes undergo dramatic morphological and molecular changes associated with alterations in their gene expression profile. Studies of white adipose tissue of obese selected mice indicates that white adipose tissue Cathepsin K mRNA was elevated 5.9-fold as were Mitf and Tfe3 (2- and 3.3-fold respectively), two transcription factors involved in Cathepsin K induction in osteoclasts. Moreover, the level of white adipose tissue Cathepsin K mRNA was increased in other obese models of mice and decreased in mice undergoing weight loss. Cathepsin K is a novel marker of obesity and can be considered a target for inhibition of adipose mass growth.

Experimental Studies

The inventors have investigated the potential of an oversulfated polysaccharide namely, calcium XPS, to act as an inhibitor of cathepsin K collagenolytic and bone resorptive activity. In particular the inventors studied the effect of an inhibitor on osteoclast formation and function.

Example 1

(i) Insoluble Bone Collagen

Fresh ovine bone was milled in a stainless steel mortar and pestle in liquid nitrogen. The resultant bone powder was defatted, decalcified and freeze-dried before storage at 4° C.

(ii) Cathepsin K Bone Collagen Digests 2 mg of insoluble bone collagen powder was digested in 100 mM sodium acetate pH 5.5 containing 2.5 mM dithiothreitol and 2.5 mM EDTA with 190 mM Cathepsin K and increasing doses of PPS.

Digestions were incubated at 37° C. for 24 hours and terminated by the addition of 2 μM $E_{84}$. Residue and supernatant were hydrolysed separately and the hydroxyproline content measured.

(iii) RAW 264.7 Cells

Murine macrophage RAW 264.7 cells respond to Receptor Activator $NF_KB$ Ligand (RANKL) stimulation to generate bone pit resorptive osteoclasts.

RAW cells were pre-cultured for several days in High-Glucose Dulbecco's Modified Eagles Medium (HG-DMEM) with 10% Fetal Calf Serum (FCS).

Cells were seeded at 250,000 cells/mL in HG-DMEM/10% FCS with/without 20 mg/mL RANKL and increasing doses of PPS (0-50 μg/mL).

Cells were incubated at 37° C., 5% $CO_2$ for 4 days.

The number of multinucleated cells present in each was counted by two observers at day 2, 3 and 4. The cells were then harvested for RNA extraction and subsequent RT-PCR.

(iv) H&E Staining

Identical cultures were prepared in petri dishes containing pre-labelled slides and incubated for 4 days, after which slides were carefully rinsed in PBS, immersed in ice-old acetone and air-dried before freezing.

The slides were then stained with H&E before multinucleated osteoclasts were photographed and counted.

(v) Results

The addition of RANKL (20 ng/mL) to RAW cells resulted in significant development of multinucleated cells by day 3

Figure 2:
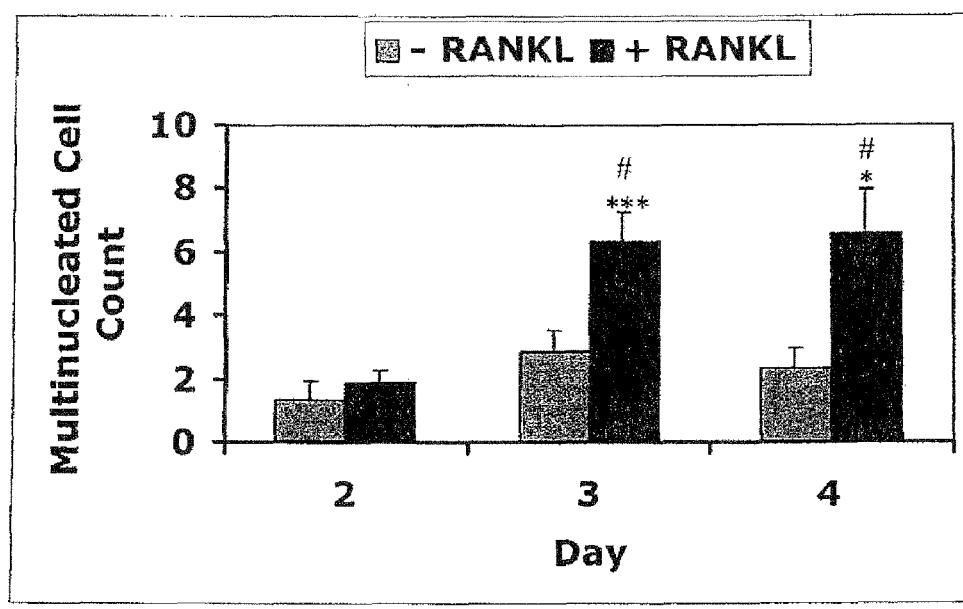
FIG. 2 is a bar graph for the results of multinucleated cell count of RAW 264.7 cell cultures±RANKL administration on day 0 (Mean±SD of cells with $\geq$2 nuclei). *=$p<0.05$ vs Day 2. ***=$p<0.0005$ vs Day 2. #=$p<0.05$, −vs+RANKL.
Figure 3:
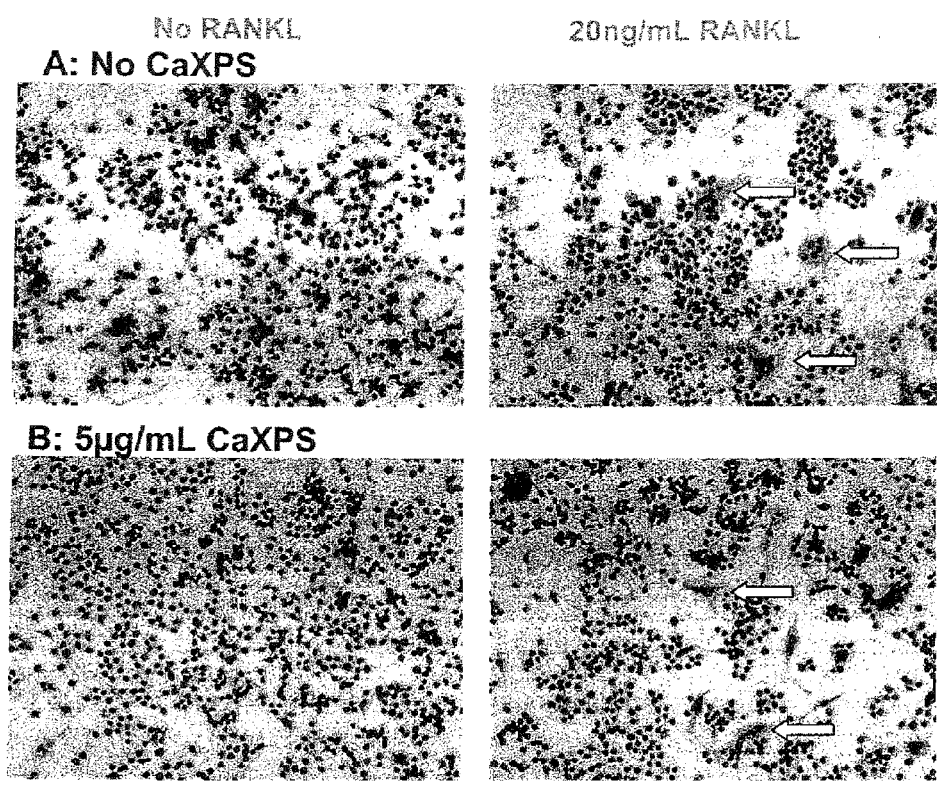
FIGS. 3A(i), (ii) and B(i), (ii) are micrographs of H&E Staining of RAW cells for counts (200× magnification). Arrows indicate multinucleated OCL cells.

(FIGS. 2 and 3; $p<0.05$), confirming RANKL is able to differentiate RAW cells into OCL cells.

Figure 4:
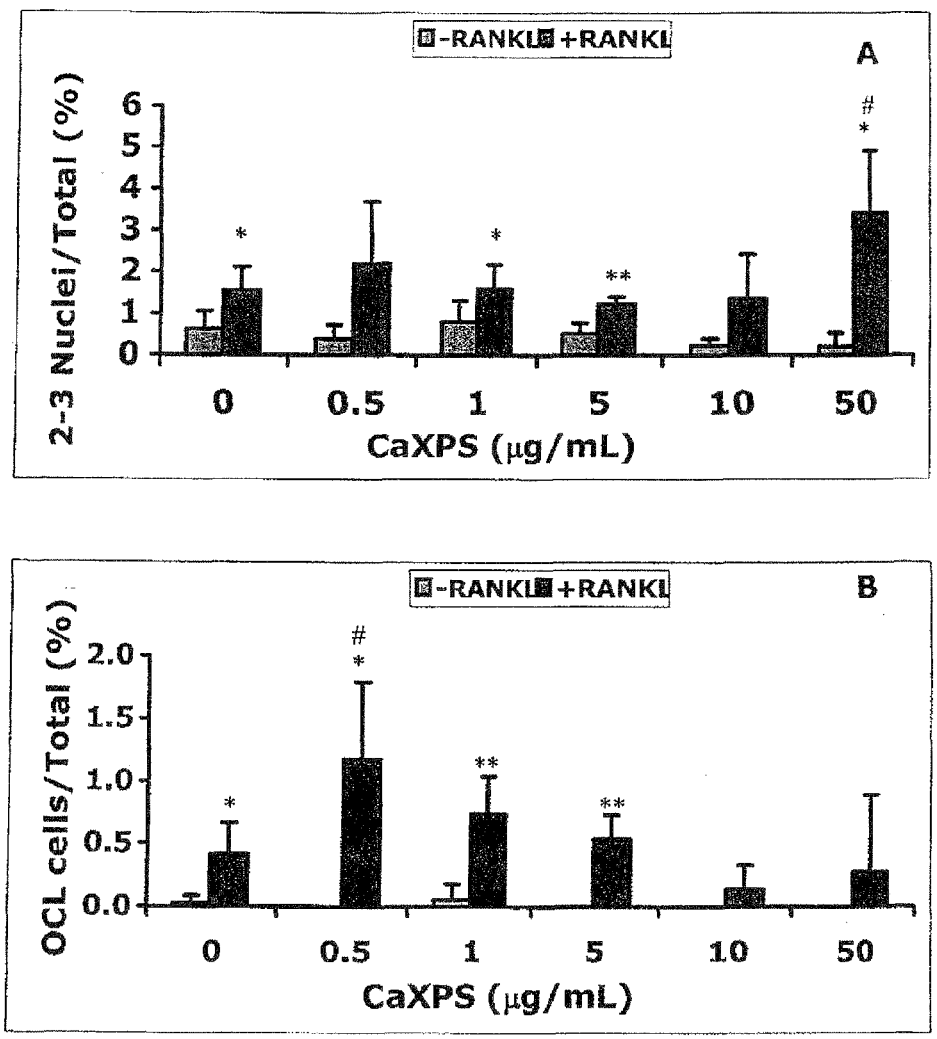
FIGS. 4 A and B are bar graphs for the results of the effect of CaXPS on the percentage of cells with (A) 2-3 nuclei and (B)>4 nuclei (OCL cells) at day 4 of RAW 264.7 cell cultures±RANKL (Mean±SD). *=$p<0.05$, −vs+RANKL. **=$p<0.005$, −vs+RANKL. #=$p<0.05$ vs no CaXPS.

FIG. 4A shows that the number of cells containing 2-3 nuclei as a percentage total cells was still significantly increased with the addition of RANKL at most concentrations of CaXPS. At 50 µg/mL CaXPS, there were significantly more 2-3 nucleated cells in the presence of RANKL ($p<0.05$).

In contrast, RANKL-induced formation of true multinucleated (>4 nuclei/cell) OCL cells was inhibited by 10 and 50 µg/mL CaXPS (FIG. 4B). Interestingly, at 0.5 µg/mL CaXPS, there was significantly more RANKL-induced multinucleated OCL cell formation than in the absence of CaXPS (FIG. 4B; $p<0.05$).

Figure 5:
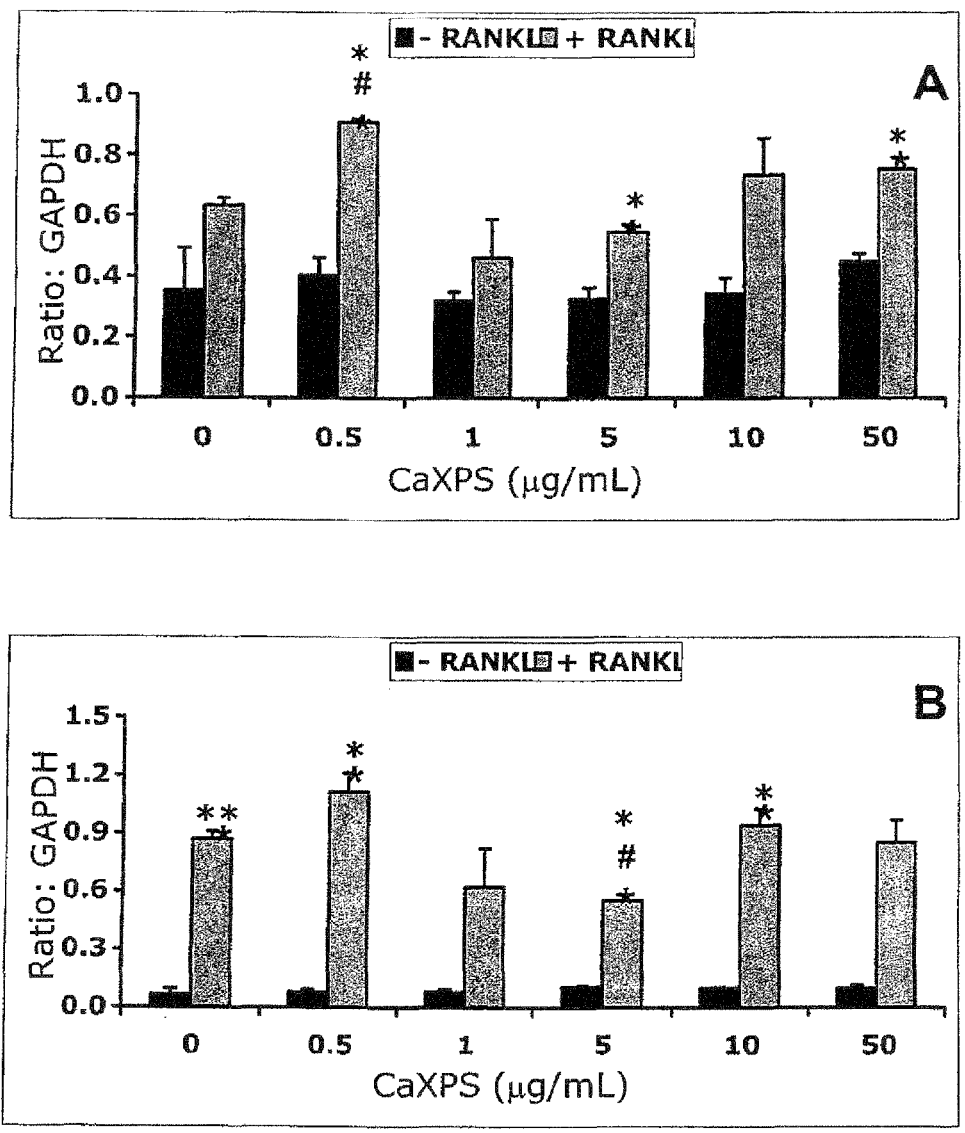
FIGS. 5A and B are bar graphs for the results of dose response of CaXPS on (A) Cathepsin K and (B) MMP9 gene expression by RAW 264.7 cells±RANKL at day 4 (Mean±SD), #=$p<0.05$ vs no CaXPS. *=$p<0.05$, −vs+RANKL. **=$p<0.005$, −vs+RANKL.
Figure 6A:
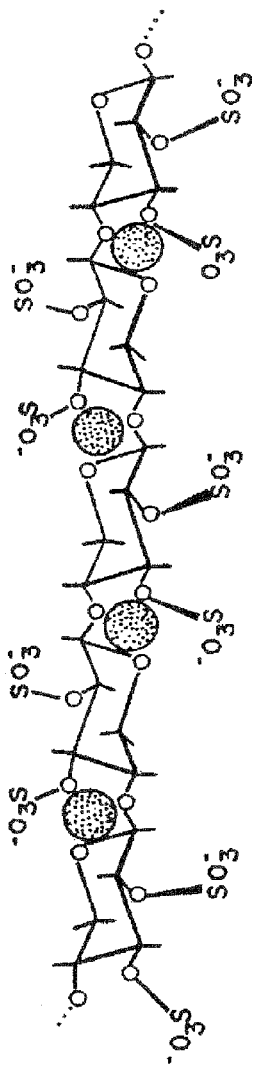
FIG. 6 is a $^{13}$C-NMR spectrum of the $^{13}$C-NMR data, the position of the zinc [A] and calcium [B] atoms in the complexes formed with Pentosan polysulfate are shown as black spheres. Note that in the zinc complex [A] the metal resides in the cleft between the pentosan rings, whereas in [B] the calcium occupies a position across the C-3 and C-5 positions of the sugar ring and close to the sulphate groups.
Figure 6B:
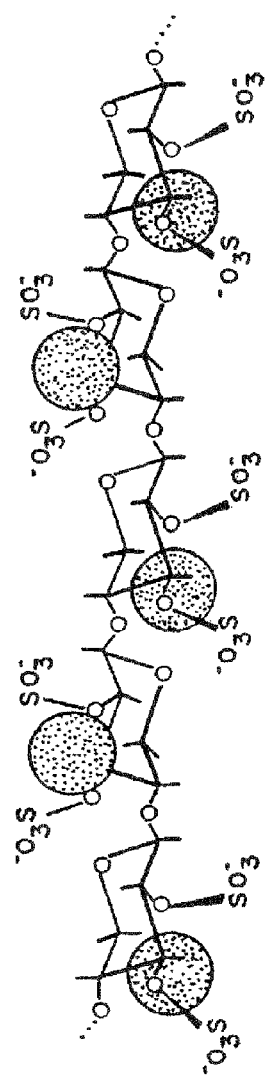

The expression of Cathepsin K (FIG. 5A) and MMP-9 (FIG. 5B) by RAW cells was increased by RANKL, which is consistent with the formation of OCL cells. Increasing concentrations of CaXPS in the absence of RANKL had no marked effect on either Cathepsin K or MMP-9 gene expression. In the presence of RANKL, a significant increase was seen in Cathepsin K expression at the lowest dose of CaXPS whereas a decrease in MMP-9 expression was seen at 5 µg/mL CaXPS ($p<0.05$).

Taken together, these results suggest the use of CaXPS in the treatment of disease through its down regulation of osteoclast formation and Cathepsin K activity. Ongoing studies will determine the effect of CaXPS on bone resorption by osteoclasts in vitro and in vivo.

The invention claimed is:

1. A method for treating or ameliorating a bone defect, wherein the bone defect is the result of a post-traumatic injury or a delayed healing or non-union of bone fractures in a mammal in need of such treatment, comprising
   the step of administering an amount of an oversulfated polysaccharide effective to inhibit cathepsin K, and thereby treat or ameliorate the bone defect, wherein the bone defect is the result of a post-traumatic injury or a delayed healing or non-union of bone fractures,
   wherein the effective amount an oversulfated polysaccharide is 0.1-30 mg/kg of body weight,
   wherein the oversulfated polysaccharide is selected from the group consisting of calcium xylopyranose polysulfate and calcium pentosan polysulfate.

2. The method according to claim 1, wherein the oversulfated polysaccharide is calcium xylopyranose polysulfate.

3. The method according to claim 1, wherein the oversulfated polysaccharide is calcium pentosan polysulfate.

* * * * *